US010239171B2

(12) United States Patent
Sato (10) Patent No.: US 10,239,171 B2
(45) Date of Patent: Mar. 26, 2019

(54) CUTTING APPARATUS (71) Applicant: Roland DG Corporation, Hamamatsu-shi, Shizuoka (JP)

(72) Inventor: Ryo Sato, Hamamatsu (JP)

(73) Assignee: ROLAND DG CORPORATION, Shizuoka (JP)

(*) Notice: Subject to any disclaimer, the term of this patent is extended or adjusted under 35 U.S.C. 154(b) by 162 days.

(21) Appl. No.: 15/623,900

(22) Filed: Jun. 15, 2017

(65) Prior Publication Data

US 2017/0361410 A1 Dec. 21, 2017

(30) Foreign Application Priority Data

Jun. 16, 2016 (JP) .................................. 2016-119696

(51) Int. Cl.
*B23Q 3/157* (2006.01)
*B23Q 3/155* (2006.01)
*A61C 13/00* (2006.01)

(52) U.S. Cl.
CPC .......... *B23Q 3/15536* (2016.11); *A61C 13/00* (2013.01); *B23Q 2003/15527* (2016.11);
(Continued)

(58) Field of Classification Search
CPC ............ Y10T 483/1809; Y10T 483/18; B23Q 2003/15527; B23Q 3/15536; B23Q 3/155–3/15793
(Continued)

(56) References Cited

U.S. PATENT DOCUMENTS 3,663,998 A * 5/1972 Cupler, II ................ B23Q 3/15
 408/31
3,722,078 A * 3/1973 Cupler, II ................ B23Q 3/15
 29/441.1
(Continued)

FOREIGN PATENT DOCUMENTS

DE 202015008056 U1 * 4/2017
JP 2010-042458 A * 2/2010
(Continued)

OTHER PUBLICATIONS

Machine Translation DE 202015008056 U1, which DE '056 was published Apr. 2017.*
(Continued)

*Primary Examiner* — Erica E Cadugan
(74) *Attorney, Agent, or Firm* — Keating & Bennett, LLP (57) ABSTRACT A cutting apparatus includes a magazine including a holder to hold a machining tool. The holder includes a container, a magnetic body, and an intermediate member. The container holds a flange of the machining tool. The container includes in its bottom surface a first insertion hole through which a tool body of the machining tool is to be inserted. The magnetic body is disposed under the container. The magnetic body includes a second insertion hole through which the tool body is to be inserted. The intermediate member is disposed inside the second insertion hole. The intermediate member includes a third insertion hole through which the tool body is to be inserted. A length of the intermediate member in a height direction is equal to or longer than a length of the magnetic body in the height direction. The intermediate member is made of a non-magnetic material.

9 Claims, 7 Drawing Sheets (52) U.S. Cl.
CPC ........ *Y10T 483/1793* (2015.01); *Y10T 483/18* (2015.01); *Y10T 483/1809* (2015.01)

(58) Field of Classification Search
USPC ..................................... 483/59, 58; 211/70.6
See application file for complete search history.

(56) References Cited

U.S. PATENT DOCUMENTS

| | | | | |
|---|---|---|---|---|
| 5,028,901 | A * | 7/1991 | Enderle | B23Q 3/15526 33/561 |
| 5,674,170 | A * | 10/1997 | Girardin | B23Q 3/15526 211/1.55 |
| 9,265,592 | B2 * | 2/2016 | Koch | A61C 13/0003 |
| 2018/0079040 | A1 * | 3/2018 | Ueda | B23Q 17/2428 |

FOREIGN PATENT DOCUMENTS

| | | | |
|---|---|---|---|
| JP | 2012-096345 A | * | 5/2012 |
| JP | 2013-121466 A | | 6/2013 |
| KR | 1020140124162 A | * | 10/2014 |

OTHER PUBLICATIONS

Machine Translation KR 1020140124162 A, which KR '162 was published Oct. 2014.*

* cited by examiner

CUTTING APPARATUS

CROSS REFERENCE TO RELATED APPLICATIONS

This application claims the benefit of priority to Japanese Patent Application No. 2016-119696 filed on Jun. 16, 2016. The entire contents of this application are hereby incorporated herein by reference.

BACKGROUND OF THE INVENTION

1. Field of the Invention

The present invention relates to cutting apparatuses.

2. Description of the Related Art

A cutting apparatus known in the related art is configured to cut a workpiece with a rotatable machining tool. A cutting apparatus of this type is configured to bring the machining tool into contact with the workpiece at a predetermined angle while three-dimensionally changing the relative positions of the workpiece and the machining tool, thus cutting the workpiece into a desired shape.

JP 2013-121466 A, for example, discloses a cutting apparatus of the type described above. A cutting apparatus of the type disclosed in JP 2013-121466 A may include an automatic tool changer (ATC) in order to automatically and continuously carry out various cutting processes with a single operation. The automatic tool changer automatically changes machining tools having differently shaped cutting edges.

Figure 7:
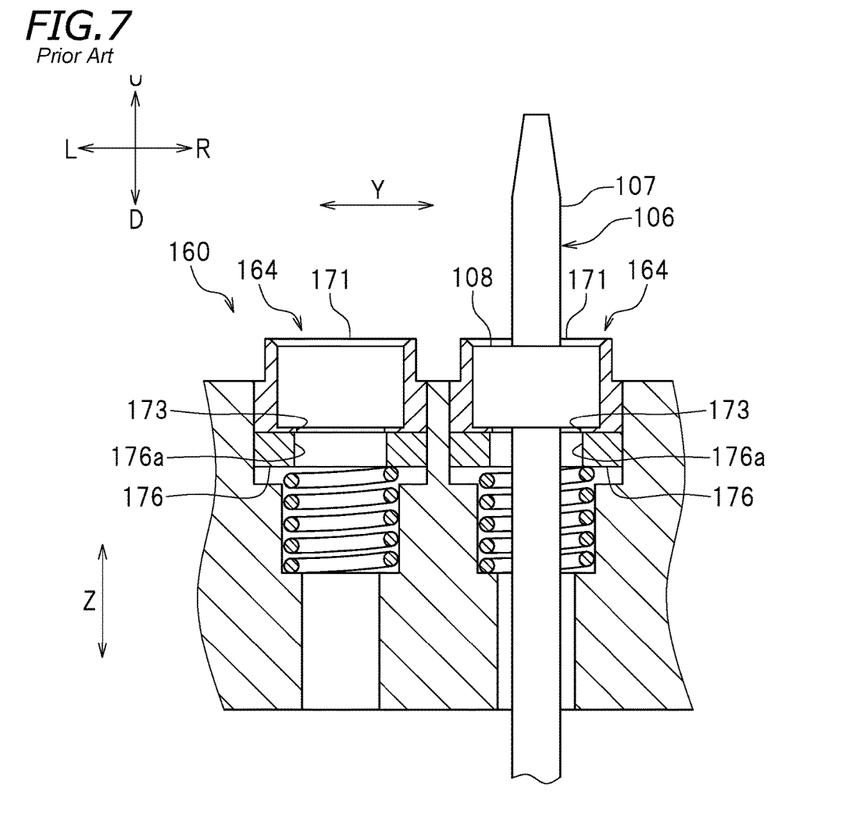
FIG. 7 is a partially enlarged front cross-sectional view of a magazine known in the art.

As illustrated in FIG. 7, a cutting apparatus of the type described above includes a magazine 160. The magazine 160 includes holders 164. Each holder 164 holds an associated one of a plurality of machining tools 106. Each machining tool 106 includes a rod tool body 107 and a flange 108 provided on the tool body 107. Each holder 164 of the magazine 160 includes a container 171 and a magnet 176. The flange 108 of each machining tool 106 is fitted into the associated container 171. The bottom surface of each container 171 is provided with an insertion hole 173. Each magnet 176 is disposed under the associated container 171. Each magnet 176 is provided with an insertion hole 176a passing through the magnet 176 in a height direction Z.

The holders 164 of the magazine 160 illustrated in FIG. 7 are configured so that the rod tool body 107 of each machining tool 106 is inserted through the insertion hole 173 of the associated container 171 and the insertion hole 176a of the associated magnet 176. The flange 108 of each machining tool 106 is fitted into the associated container 171. Thus, each machining tool 106 is held in the associated holder 164.

The tool body 107 of each machining tool 106 may be made of a magnetic material, such as iron. Suppose that a user tries to manually hold the machining tool 106, including the tool body 107 made of a magnetic material, in the associated holder 164 of the magazine 160 illustrated in FIG. 7. In such a case, the tool body 107 of the machining tool 106 may be attracted by the magnet 176 of the associated holder 164. The machining tool 106 attracted by the magnet 176 may come into contact with the magnet 176. Thus, the magnetic force of the magnet 176 may make it difficult to appropriately hold the machining tool 106 in the holder 164 of the magazine 160.

SUMMARY OF THE INVENTION

Accordingly, preferred embodiments of the invention provide a cutting apparatus that enables a user to manually hold a machining tool in a magazine with ease.

A cutting apparatus according to a preferred embodiment of the invention is able to cut a workpiece by rotating a machining tool including a rod tool body and a flange disposed on the tool body. The cutting apparatus includes a magazine including a holder to hold the machining tool. The holder includes a container, a magnetic body, and an intermediate member. The container holds the flange. The container includes in its bottom surface a first insertion hole through which the tool body is to be inserted. The magnetic body is disposed under the container. The magnetic body includes a second insertion hole through which the tool body is to be inserted. The intermediate member is disposed inside the second insertion hole of the magnetic body. The intermediate member includes a third insertion hole through which the tool body is to be inserted. Assuming that a direction in which the machining tool is to be inserted into the holder is a first direction, a length of the intermediate member in the first direction is equal to or longer than a length of the magnetic body in the first direction. The intermediate member is made of a non-magnetic material.

The cutting apparatus according to this preferred embodiment has a structure such that, with the machining tool held in the holder of the magazine, the intermediate member made of a non-magnetic material is located between the tool body of the machining tool and the magnetic body. Thus, when a user attempts to manually hold the machining tool in the holder of the magazine, the intermediate member prevents the tool body from being attracted by the magnetic force of the magnetic body. Consequently, this preferred embodiment enables the user to manually hold the machining tool in the holder with ease.

Various preferred embodiments of the present invention provide a cutting apparatus that enables a user to manually hold a machining tool in a magazine with ease.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

A cutting apparatus 100 according to a preferred embodiment of the present invention will be described below with reference to the drawings. The preferred embodiments described below are not intended to limit the present invention in any way. Components and elements having the same functions are identified by the same reference signs, and description thereof will be simplified or omitted when deemed redundant.

Figure 1:
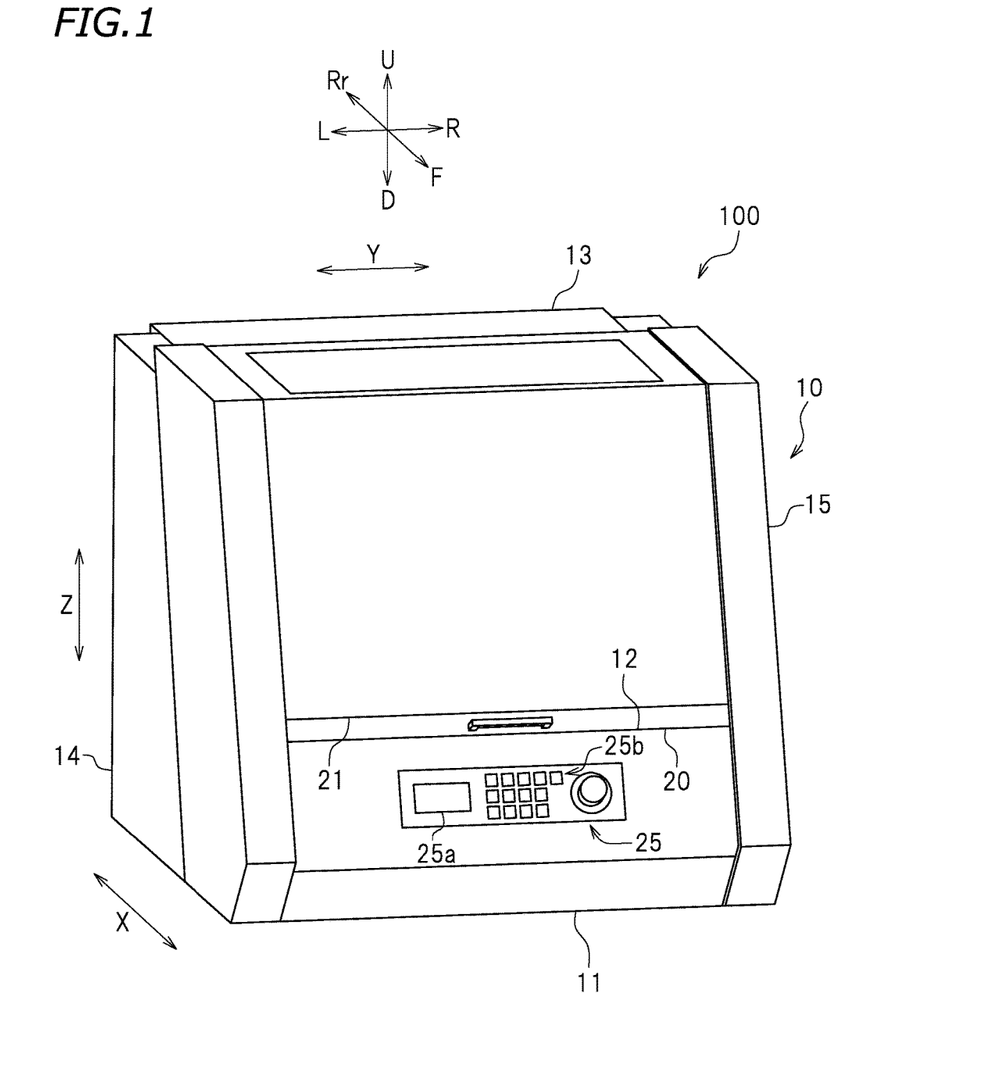
FIG. 1 is a perspective view of the cutting apparatus according to a preferred embodiment of the present invention.
Figure 2:
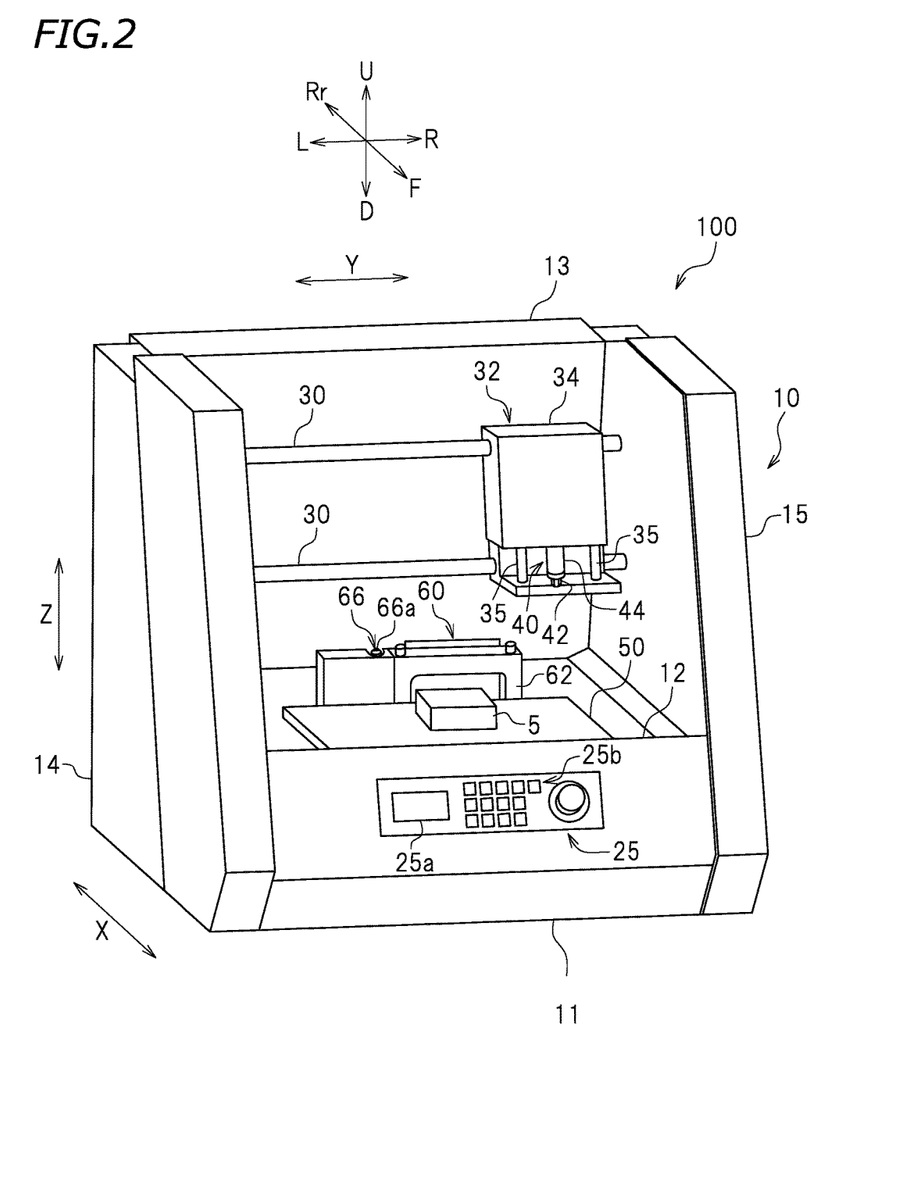
FIG. 2 is a perspective view of the cutting apparatus, with its front cover removed.

FIG. 1 is a perspective view of the cutting apparatus 100 according to the present preferred embodiment of the present invention. FIG. 2 is a perspective view of the cutting apparatus 100, with its front cover 20 removed. The following description is based on the assumption that when a user faces the front of the cutting apparatus 100, the direction toward the user is a forward direction, and the direction away from the user is a rearward direction. The terms "right", "left", "up", and "down" respectively refer to right, left, up, and down with respect to the user facing the front of the cutting apparatus 100. The reference signs F, Rr, R, L, U, and D in the drawings respectively represent front, rear, right, left, up, and down. These directions are defined merely for the sake of convenience of description and do not limit in any way how the cutting apparatus 100 may be installed or how the invention may be practiced. The reference sign Y in the drawings represents a main scanning direction. In this preferred embodiment, the main scanning direction Y is a right-left direction. The reference sign X in the drawings represents a sub-scanning direction. In this preferred embodiment, the sub-scanning direction X is a front-rear direction. The main scanning direction Y and the sub-scanning direction X are perpendicular to each other in a plan view. The reference sign Z in the drawings represents a height direction, i.e., an up-down direction. The main scanning direction Y, the sub-scanning direction X, and the height direction Z may be any other suitable directions. The main scanning direction Y, the sub-scanning direction X, and the height direction Z may be appropriately set in accordance with the configuration or shape of the cutting apparatus 100. In this preferred embodiment, the height direction Z is a direction in which machining tools 6 (see FIG. 3) are to be inserted into holders 64 (see FIG. 3). The machining tools 6 and the holders 64 will be described below. The height direction Z corresponds to a "first direction". The main scanning direction Y is perpendicular to the height direction Z in a front view. The main scanning direction Y corresponds to a "second direction".

Figure 3:
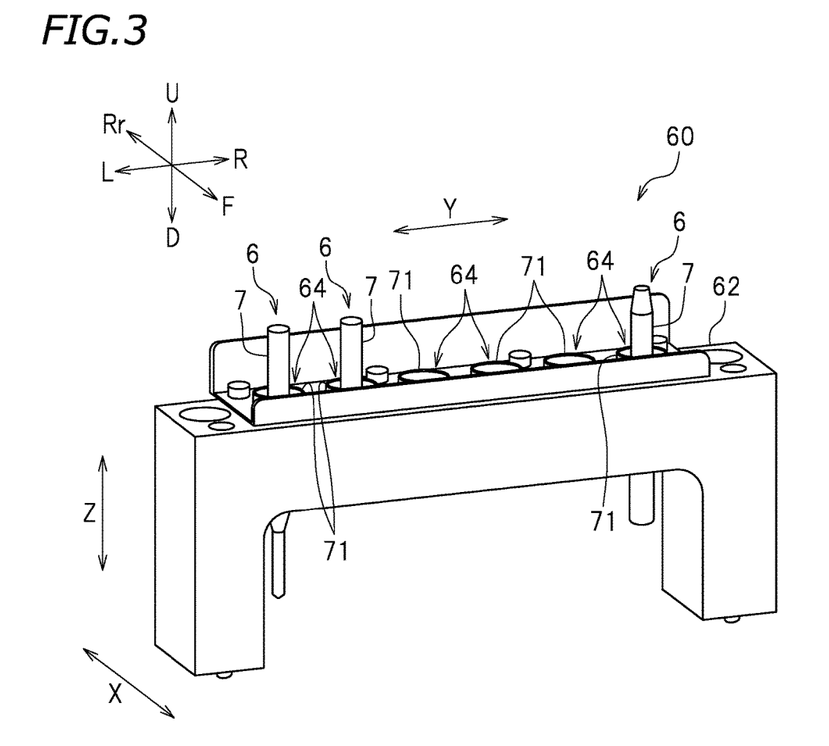
FIG. 3 is a perspective view of a magazine.

As illustrated in FIG. 2, the cutting apparatus 100 is able to cut a workpiece 5 (which is to be cut) by rotating the machining tool 6 (see FIG. 3). In this preferred embodiment, the cutting apparatus 100 preferably has a box shape. As illustrated in FIG. 1, the cutting apparatus 100 includes a case 10, the front cover 20, and an operation panel 25. As illustrated in FIG. 2, the front portion of the case 10 is provided with an opening. The case 10 includes a base 11, a front wall 12, a rear wall 13, a left wall 14, and a right wall 15. The base 11 is a plate member. The front wall 12 is connected to the front end of the base 11. The front wall 12 extends upward from the base 11. The rear wall 13 is connected to the rear end of the base 11. The rear wall 13 extends upward from the base 11. The left wall 14 is connected to the left end of the base 11. The left wall 14 extends upward from the base 11. The lower front end of the left wall 14 is connected to the left end of the front wall 12. The rear end of the left wall 14 is connected to the left end of the rear wall 13. The right wall 15 is connected to the right end of the base 11. The right wall 15 extends upward from the base 11. The lower front end of the right wall 15 is connected to the right end of the front wall 12. The rear end of the right wall 15 is connected to the right end of the rear wall 13.

As illustrated in FIG. 1, the front cover 20 is provided such that the opening in the front portion of the case 10 is openable and closable. In one example, the front cover 20 is supported by the case 10 such that the front cover 20 is rotatable around its rear end. In this preferred embodiment, the front cover 20 is provided with a window 21. The window 21 is a transparent acrylic plate, for example. The transparent window 21 enables the user to visually recognize the inside of the cutting apparatus 100 through the window 21.

The operation panel 25 is provided in the center of the front wall 12 of the case 10. The user operates the operation panel 25 in performing a cutting-related operation. The operation panel 25 includes a display 25a and an input interface 25b. The display 25a presents cutting-related formation, such as the time required for cutting and a cutting status. The user enters cutting-related information through the input interface 25b.

The internal arrangement of the cutting apparatus 100 will be described below. As illustrated in FIG. 2, the cutting apparatus 100 includes a pair of first guide rails 30, a carriage 32, a cutting head 40, a table 50, a magazine 60, and a controller 80 (see FIG. 6).

The first guide rails 30 guide the machining tool 6 (see FIG. 3) mounted on the cutting head 40 in the main scanning direction Y. In this preferred embodiment, the number of first guide rails 30 is two, and the two first guide rails 30 are disposed in the case 10. Each of the pair of first guide rails 30 extends in the main scanning direction Y. The left end of each first guide rail 30 is connected to the left wall 14. The right end of each first guide rail 30 is connected to the right wall 15. The pair of first guide rails 30 are disposed one above the other in the height direction Z. The number of first guide rails 30 is not limited to any particular number. The number of first guide rails 30 may be one, for example.

The carriage 32 is disposed in the case 10. The carriage 32 is slidable relative to the pair of first guide rails 30. The carriage 32 is in engagement with the pair of first guide rails 30. The carriage 32 is movable along the pair of first guide rails 30 in the main scanning direction Y. In this preferred embodiment, the carriage 32 is connected with a first motor 32A (see FIG. 6). The carriage 32 moves in the main scanning direction Y upon receiving a driving force from the first motor 32A.

Figure 6:
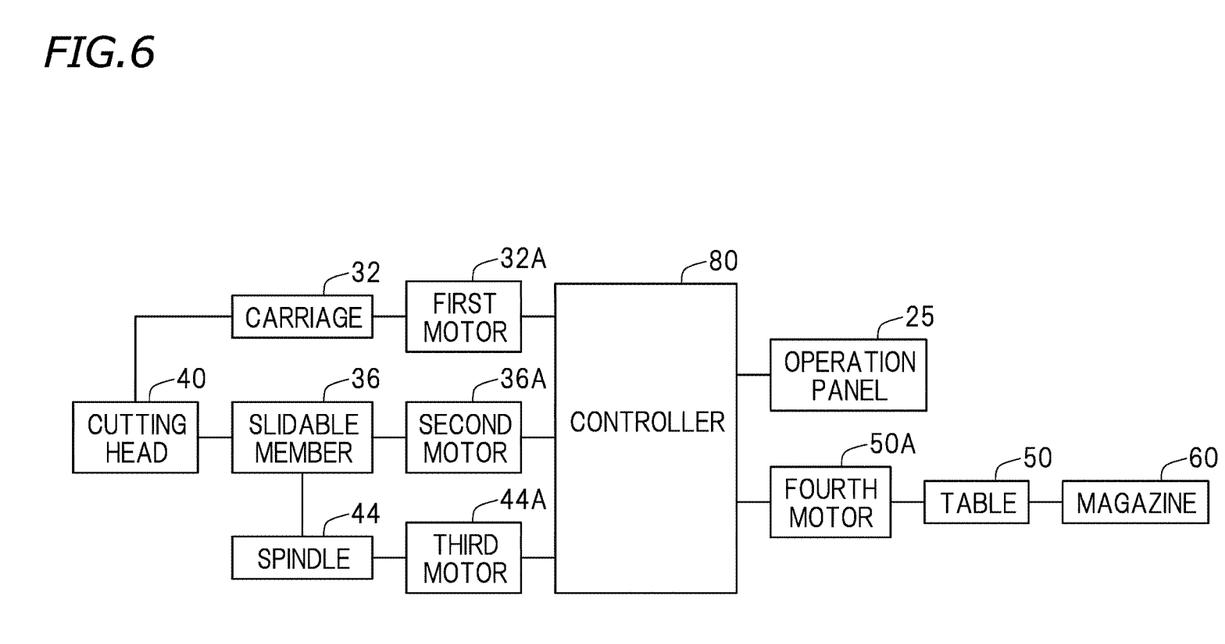
FIG. 6 is a block diagram of the cutting apparatus.

In this preferred embodiment, the carriage 32 includes a carriage casing 34, a pair of second guide rails 35, and a slidable member 36 (see FIG. 6). The carriage casing 34 is in engagement with the pair of first guide rails 30. The carriage casing 34 includes an internal space. The pair of second guide rails 35 extend in the height direction Z. The pair of second guide rails 35 are disposed in the internal space of the carriage casing 34. The slidable member 36 illustrated in FIG. 6 is slidable along the pair of second guide rails 35. The slidable member 36 is in engagement with the pair of second guide rails 35. Thus, the slidable member 36 is movable along the second guide rails 35 in the height direction Z. In this preferred embodiment, the slidable member 36 illustrated in FIG. 6 is connected with a second motor 36A (see FIG. 6). The slidable member 36 moves in the height direction Z upon receiving a driving force from the second motor 36A. Although not illustrated, the cutting head 40 is mounted on the slidable member 36.

The cutting head 40 cuts the workpiece 5 with the machining tool 6 (see FIG. 3). Movement of the slidable member 36 (see FIG. 6) in the height direction Z causes the cutting head 40 to move along the pair of second guide rails 35 in the height direction Z. In this preferred embodiment, the cutting head 40 includes a gripper 42 and a spindle 44.

The gripper 42 grips an upper end 7a (see FIG. 5) of the machining tool 6. Although not illustrated, the gripper 42 includes a plurality of horizontally aligned members. The gripper 42 grips the machining tool 6 by pinching the upper end 7a (see FIG. 5) of the machining tool 6 with the horizontally aligned members. As illustrated in FIG. 2, the gripper 42 according to this preferred embodiment is mounted on the lower end of the spindle 44.

The spindle 44 causes the machining tool 6 (see FIG. 5) to rotate. Specifically, the spindle 44 causes the gripper 42 to rotate, so that the machining tool 6 gripped by the gripper 42 rotates around the axis of the machining tool 6. The axis of the machining tool 6 in this case is parallel or substantially parallel to the height direction Z. The spindle 44 extends in the height direction Z. In this preferred embodiment, the spindle 44 is connected with a third motor 44A (see FIG. 6) to rotate the spindle 44. The spindle 44 rotates upon receiving a driving force from the third motor 44A. The rotation of the spindle 44 causes the machining tool 6 gripped by the gripper 42 to rotate. Although not illustrated, the spindle 44 is mounted on the slidable member 36 (see FIG. 6) slidable along the pair of second guide rails 35. The spindle 44 is rotatable relative to the slidable member 36. Thus, the movement of the slidable member 36 in the height direction Z causes the gripper 42 and the spindle 44 of the cutting head 40 and the machining tool 6 gripped by the gripper 42 to move in the height direction Z.

The workpiece 5 (which is to be cut) is placed on the table 50. The workpiece 5 placed on the table 50 undergoes cutting. The table 50 is disposed in the case 10. The table 50 is disposed below the pair of first guide rails 30, the carriage 32, and the cutting head 40. The table 50 is disposed above the base 11. The table 50 is slidable along a guide rail (not illustrated) that is provided on the base 11 and extends in the sub-scanning direction X. The table 50 is connected with a fourth motor 50A (see FIG. 6). The table 50 moves in the sub-scanning direction X upon receiving a driving force from the fourth motor 50A.

Figure 4:
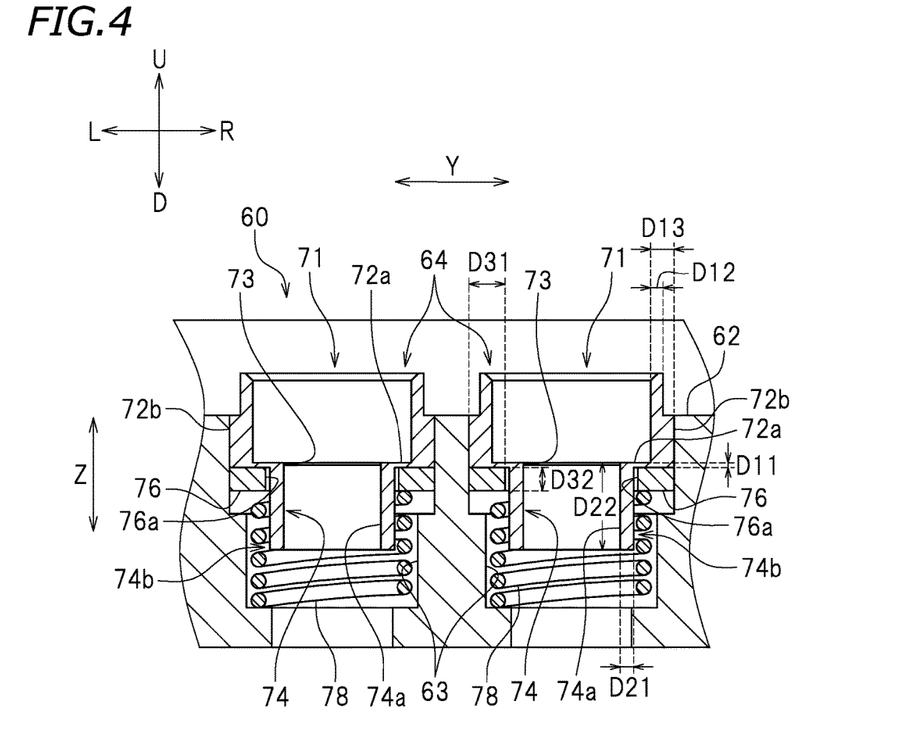
FIG. 4 is a partially enlarged front cross-sectional view of the magazine.
Figure 5:
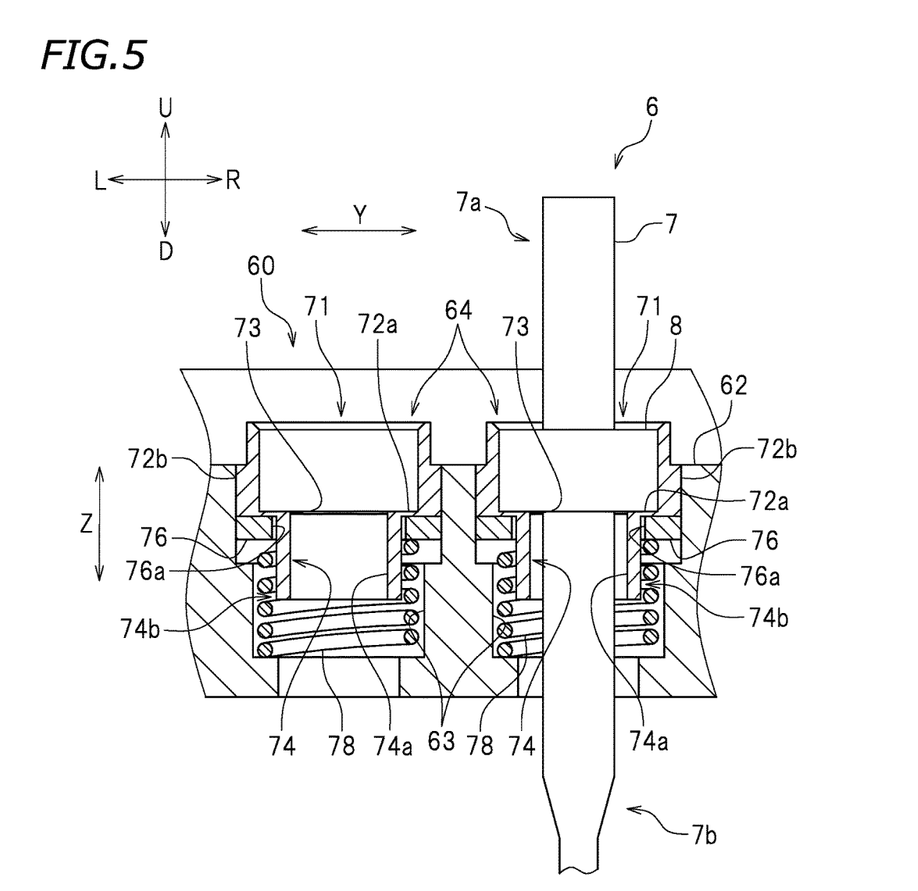
FIG. 5 is a partially enlarged front cross-sectional view of the magazine, with a machining tool held in a holder of the magazine.

The magazine 60 will be described in detail below. FIG. 3 is a perspective view of the magazine 60. FIG. 4 is a partially enlarged front cross-sectional view of the magazine 60. FIG. 5 is a partially enlarged front cross-sectional view of the magazine 60, with the machining tool 6 held in the associated holder 64 of the magazine 60. As illustrated in FIG. 3, the magazine 60 holds a plurality of the machining tools 6. In this preferred embodiment, the magazine 60 includes a magazine body 62, a plurality of the holders 64, and a tool sensor 66 (see FIG. 2). The magazine body 62 preferably has a box shape, for example.

The holders 64 hold the machining tools 6. As illustrated in FIG. 4, the upper surface of the magazine body 62 according to this preferred embodiment is provided with a plurality of holding holes 63. Each holder 64 is disposed in an associated one of the holding holes 63. Each holder 64 holds an associated one of the machining tools 6. As illustrated in FIG. 3, the magazine 60 is provided with the plurality of holders 64, so that various types of the machining tools 6 are held in the holders 64. In this preferred embodiment, the number of holders 64 is six, for example. The six holders 64 are disposed in alignment with each other in the main scanning direction Y. The number of holders 64, however, is not limited to any particular number. The number of holders 64 may be one or ten, for example. In this preferred embodiment, the holders 64 preferably have the same or substantially the same configuration. The configuration of each holder 64 will be described in detail below. As illustrated in FIG. 4, each holder 64 according to this preferred embodiment includes a container 71, an intermediate member 74, a magnetic body 76, and a spring 78.

As illustrated in FIG. 5, each machining tool 6 includes a flange 8, and the flange 8 of each machining tool 6 is held in the associated container 71. Each container 71 is held in the associated holding hole 63 of the magazine body 62. As illustrated in FIG. 4, each container 71 according to this preferred embodiment includes a bottom plate 72a and a side plate 72b. The bottom plate 72a preferably is a circular or substantially circular plate. The bottom surface of the container 71 (or more specifically, the central portion of the bottom plate 72a) is provided with a first insertion hole 73. The side plate 72b extends upward from the end of the bottom plate 72a. More specifically, the side plate 72b is connected to the outer edge of the bottom plate 72a and extended upward from the outer edge of the bottom plate 72a. The side plate 72b preferably has a cylindrical or substantially cylindrical shape. As illustrated in FIG. 5, the flange 8 of the machining tool 6 according to this preferred embodiment is held in a space defined by the bottom plate 72a and the side plate 72b of the associated container 71. Each container 71 conforms in shape to the flange 8 of the associated machining tool 6. The bottom plate 72a and the side plate 72b of each container 71 are integral with each other.

With the machining tool 6 held in the holder 64, the intermediate member 74 prevents a magnetic force generated by the magnetic body 76 from attracting a tool body 7 of the machining tool 6 to the magnetic body 76. In other words, with the machining tool 6 held in the holder 64, the intermediate member 74 prevents the machining tool 6 from coming into direct contact with the magnetic body 76. The intermediate member 74 preferably has a cylindrical or substantially cylindrical shape extending in the height direction Z. A portion of the intermediate member 74 located centrally in the plan view is provided with a third insertion hole 74a passing through the intermediate member 74 in the height direction Z. The tool body 7 of the machining tool 6 is inserted through the third insertion hole 74a. The intermediate member 74 is held in the holding hole 63 of the magazine body 62. In this preferred embodiment, the intermediate member 74 is provided under the container 71. The intermediate member 74 is connected to the underside of the bottom plate 72a. Specifically, the intermediate member 74 extends downward from the inner edge of the bottom plate 72a of the container 71. The upper end of the intermediate member 74 is continuous with the inner edge of the bottom plate 72a. In this preferred embodiment, the intermediate member 74 is integral with the container 71. In other words, the container 71 and the intermediate member 74 define a single unit.

The intermediate member 74 and the bottom plate 72a and the side plate 72b of the container 71 are made of a non-magnetic material. As used herein, the term "non-magnetic material" refers to a material that generates no magnetic force and does not attract a magnetic member.

It is to be noted that the term "non-magnetic material" may herein refer to a feebly magnetic material that generates a magnetic force only to a degree that does not attract a magnetic member. In this preferred embodiment, the intermediate member 74 and the bottom plate 72a and the side plate 72b of the container 71 are preferably made of brass, for example. Alternatively, the intermediate member 74 and the bottom plate 72a and the side plate 72b of the container 71 may be made of resin.

The magnetic body 76 is a magnetic member. The magnetic body 76 is not limited to any particular type of magnetic body. In this preferred embodiment, the magnetic body 76 is a magnet, for example. The magnetic body 76 is held in the holding hole 63 of the magazine body 62. The magnetic body 76 is disposed under the container 71. The magnetic body 76 preferably has a cylindrical or substantially cylindrical shape, for example. A portion of the magnetic body 76 located centrally in the plan view is provided with a second insertion hole 76a passing through the magnetic body 76 in the height direction Z. The intermediate member 74 is disposed inside the second insertion hole 76a of the magnetic body 76. As illustrated in FIG. 5, the tool body 7 of the machining tool 6 is inserted through the second insertion hole 76a. The magnetic body 76 is disposed outward of the intermediate member 74. The lower portion of the intermediate member 74 extends downward of the magnetic body 76. In other words, the intermediate member 74 includes a protrusion 74b protruding downward of the magnetic body 76. The diameter of the second insertion hole 76a of the magnetic body 76 is larger than the outer diameter of the intermediate member 74.

The spring 78 is an elastic member. The spring 78 is held in the holding hole 63 of the magazine body 62 such that the spring 78 exerts an upward elastic force. The spring 78 is not limited to any particular type of spring. In this preferred embodiment, the spring 78 is a coiled spring. Specifically, the spring 78 is coiled such that a predetermined inner space is defined. The spring 78 is disposed below the container 71 and the magnetic body 76. As previously mentioned, the protrusion 74b of the intermediate member 74 extends downward of the magnetic body 76. At least a portion of the spring 78 is disposed around the protrusion 74b of the intermediate member 74. The spring 78 is not limited to any particular material. The spring 78 according to this preferred embodiment is preferably made of a non-magnetic material. In one example, the spring 78 is preferably made of stainless steel.

The relationships between the dimensions of the container 71, the intermediate member 74, and the magnetic body 76 will be described below. As illustrated in FIG. 4, in this preferred embodiment, a thickness D11 of the bottom plate 72a of the container 71 in the height direction Z is smaller than a first horizontal thickness D12 of the side plate 72b of the container 71. As used herein, the term "first horizontal thickness D12" refers to the smallest horizontal thickness of the side plate 72b. Note that the side plate 72b of the container 71 further has a second horizontal thickness D13 larger than the first horizontal thickness D12. As used herein, the term "second horizontal thickness D13" refers to the largest horizontal thickness of the side plate 72b. A thickness D21 of the intermediate member 74 in the horizontal direction (i.e., the main scanning direction Y in FIG. 4) is larger than the thickness D11 of the bottom plate 72a and the first horizontal thickness D12 of the side plate 72b. The thickness D21 of the intermediate member 74 is smaller than the second horizontal thickness D13 of the side plate 72b. As used herein, the term "thickness D21 of the intermediate member 74" refers to a length between the inner and outer diameters of the intermediate member 74 in the main scanning direction Y in the front view. A length D22 of the intermediate member 74 in the height direction Z is equal to or longer than a length D32 of the magnetic body 76 in the height direction Z. A length D31 of the magnetic body 76 in the horizontal direction (i.e., the main scanning direction Y in FIG. 4) is longer than the length D32 of the magnetic body 76 in the height direction Z. As used herein, the term "length D31 of the magnetic body 76" refers to a distance between the inner and outer diameters of the magnetic body 76 in the main scanning direction Y in the front view. The length D31 of the magnetic body 76 is longer than the length D32 of the magnetic body 76 measured in the axial direction of the machining tool 6 held in the holder 64.

As illustrated in FIG. 2, the magazine 60 according to this preferred embodiment is provided with the tool sensor 66. The tool sensor 66 detects whether the machining tool 6 (see FIG. 5) is gripped by the gripper 42 of the cutting head 40. The tool sensor 66 detects contact of the machining tool 6 with the tool sensor 66 so as to determine whether the machining tool 6 is gripped by the gripper 42. A method for detecting contact of the machining tool 6 by the tool sensor 66 is not limited to any particular method. In this preferred embodiment, the tool sensor 66 preferably has a columnar shape, for example. The upper surface of the tool sensor 66 is provided with a convex portion. The convex portion protrudes upward of the upper surface of the magazine body 62. The convex portion of the tool sensor 66 is provided with a contact sensor including a switch 66a. The switch 66a is mechanically changeable between on and off states. In one example, the contact sensor has a structure such that a minute displacement of the upper surface of the switch 66a caused by a minute load mechanically changes the switch 66a between on and off states. The tool sensor 66 detects contact of the machining tool 6 when the switch 66a is turned on or off.

In this preferred embodiment, the magazine 60 is secured to the table 50. Specifically, the magazine body 62 of the magazine 60 is provided on the rear end of the table 50. The magazine 60, however, may be provided at any other location. In one example, the magazine 60 may be provided on the right or left end of the table 50. In this preferred embodiment, the magazine 60 is movable in the sub-scanning direction X together with the table 50. The table 50 moves in the sub-scanning direction X upon receiving a driving force from the fourth motor 50A (see FIG. 6) connected to the table 50. The movement of the table 50 in the sub-scanning direction X causes the magazine 60 to move in the sub-scanning direction X.

The machining tool 6 to be gripped by the gripper 42 of the cutting head 40 will be described below. Cutting performed by the cutting apparatus 100 involves use of the machining tools 6. As illustrated in FIG. 5, each machining tool 6 includes the tool body 7 and the flange 8. The tool body 7 has a rod shape. The flange 8 is provided on the tool body 7. In this preferred embodiment, the flange 8 is provided on a portion of the tool body 7 above the vertical center of the tool body 7. The flange 8 extends outward from the tool body 7. The flange 8 has a columnar shape, for example. The flange 8 is provided on the tool body 7 such that the flange 8 surrounds the tool body 7 in the plan view. When the machining tool 6 is held in the holder 64 of the magazine 60, the flange 8 is held in the container 71. In other words, when the machining tool 6 is held in the holder 64, the flange 8 is fitted into the container 71. Accordingly, the flange 8 conforms in shape to the container 71. With the flange 8 of the machining tool 6 inserted into the container 71, the upper end 7a of the tool body 7 located above the flange 8 protrudes from the container 71. The upper end 7a is to be gripped by the gripper 42 (see FIG. 2). A portion of the tool body 7 located below the flange 8 is provided with a cutter 7b. In this preferred embodiment, the cutters 7b of the machining tools 6 have various shapes. The machining tools 6 are not limited to any particular material. In this preferred embodiment, the tool body 7 and the flange 8 of each machining tool 6 are made of a magnetic material. In one example, the tool body 7 is made of iron, for example. The surface of the flange 8 may be made of aluminum, for example.

The controller 80 according to this preferred embodiment will be described below. FIG. 6 is a block diagram of the cutting apparatus 100. The controller 80 is programmed or configured to control cutting. The controller 80 is preferably provided in the cutting apparatus 100. The controller 80, however, may be provided at any other location. The controller 80 is not limited to any particular configuration. In one example, the controller 80 may be a computer and may include a central processing unit (CPU), a read-only memory (ROM) storing, for example, program(s) to be executed by the CPU, and a random-access memory (RAM).

The controller 80 is connected to the operation panel 25. The user operates the operation panel 25 so as to transmit a signal from the operation panel 25 to the controller 80. The controller 80 carries out control of cutting in accordance with the signal received from the operation panel 25. The controller 80 is connected to the first motor 32A. The first motor 32A is connected to the carriage 32. The controller 80 controls driving of the first motor 32A so as to control movement of the carriage 32 and the cutting head 40 in the main scanning direction Y. The controller 80 is connected to the second motor 36A. The second motor 36A is connected to the slidable member 36 on which the cutting head 40 is mounted. The controller 80 controls driving of the second motor 36A so as to control movement of the cutting head 40 in the height direction Z. The controller 80 is connected to the third motor 44A. The third motor 44A is connected to the spindle 44. The controller 80 controls driving of the third motor 44A so as to control rotation of the spindle 44 and the machining tool 6 gripped by the gripper 42. The controller 80 is connected to the fourth motor 50A. The fourth motor 50A is connected to the table 50. The controller 80 controls driving of the fourth motor 50A so as to control movement of the table 50 and the magazine 60 secured to the table 50 in the sub-scanning direction X. Although not illustrated, the controller 80 is connected to the switch 66a (see FIG. 2) of the tool sensor 66. The controller 80 detects turning on or off of the switch 66a so as to detect whether the machining tool 6 gripped by the gripper 42 has come into contact with the switch 66a.

The preceding paragraph has described an example of the controller 80 according to the present preferred embodiment. The following description briefly discusses the procedure of holding the machining tool 6, gripped by the gripper 42 of the cutting head 40, in the holder 64 of the magazine 60. First, with the machining tool 6 gripped by the gripper 42, the controller 80 three-dimensionally moves the cutting head 40 relative to the magazine 60. Specifically, the controller 80 drives the first motor 32A (see FIG. 6) so as to cause the cutting head 40 to move along the pair of first guide rails 30 in the main scanning direction Y as illustrated in FIG. 2. Thus, the cutting head 40 moves relative to the magazine 60 in the main scanning direction Y. The controller 80 drives the second motor 36A (see FIG. 6) so as to cause the cutting head 40 to move along the pair of second guide rails 35 in the height direction Z. Thus, the cutting head 40 moves relative to the magazine 60 in the height direction Z. The controller 80 drives the fourth motor 50A (see FIG. 6) so as to cause the table 50 and the magazine 60 to move in the sub-scanning direction X. Thus, the cutting head 40 moves relative to the magazine 60 in the sub-scanning direction X.

The controller 80 causes the cutting head 40 to move relative to the magazine 60 such that the gripper 42 of the cutting head 40 is located over an associated one of the holders 64 of the magazine 60 in which the machining tool 6 is to be held. The controller 80 then controls driving of the second motor 36A so as to move the cutting head 40 downward. Thus, the machining tool 6 gripped by the gripper 42 is held in the associated holder 64 of the magazine 60 as illustrated in FIG. 5. Specifically, the flange 8 of the machining tool 6 is held in the container 71 of the holder 64. The cutter 7b of the tool body 7 of the machining tool 6 is inserted through the first insertion hole 73 of the bottom plate 72a of the container 71, the third insertion hole 74a of the intermediate member 74, the second insertion hole 76a of the magnetic body 76, and the inner space of the spring 78. In the course of the insertion, the cutter 7b of the tool body 7 does not come into contact with the magnetic body 76 or the spring 78. The intermediate member 74 is located between the tool body 7 of the machining tool 6 and the magnetic body 76 and between the tool body 7 and a portion of the spring 78. When the machining tool 6 is held in the holder 64, the machining tool 6 is preferably pushed down into the holder 64. In this case, with the flange 8 of the machining tool 6 in intimate contact with the bottom plate 72a of the container 71, the machining tool 6 is pushed back by an upward elastic force exerted by the spring 78, so that the machining tool 6 is held at an appropriate position. With the machining tool 6 thus held in the holder 64, the gripper 42 releases the machining tool 6. This completes the procedure of holding the machining tool 6 in the holder 64.

When no cutting is being performed on the workpiece 5, this preferred embodiment allows the user to manually hold the machining tool 6 in the holder 64 of the magazine 60. When no cutting is being performed on the workpiece 5, the user is also allowed to manually pull out the machining tool 6, which is held in the holder 64, from the holder 64. In this preferred embodiment, with the machining tool 6 held in the holder 64 of the magazine 60, the intermediate member 74 made of a non-magnetic material is located between the tool body 7 of the machining tool 6 and the magnetic body 76 as illustrated in FIG. 5. This prevents or reduces generation of magnetic force in the inner space of the intermediate member 74 when the user attempts to manually hold the machining tool 6 in the holder 64 of the magazine 60. Thus, the tool body 7 is prevented from being attracted by the magnetic force of the magnetic body 76. Accordingly, the user manually holds the machining tool 6 in the holder 64 with ease. Because generation of magnetic force in the inner space of the intermediate member 74 is prevented or reduced, the user manually pulls out the machining tool 6, which is held in the holder 64, from the holder 64 with ease.

In this preferred embodiment, the container 71 and the intermediate member 74 are integral with each other. The container 71 includes the side plate 72b extending upward from the end of the bottom plate 72a provided with the first insertion hole 73. The intermediate member 74 is connected to the underside of the bottom plate 72a. The container 71 and the intermediate member 74 thus define a single unit. Consequently, this preferred embodiment reduces the number of components.

As illustrated in FIG. 4, the thickness D21 of the intermediate member 74 in the main scanning direction Y in the front view is larger than the thickness D11 of the bottom plate 72a in the height direction Z. Thus, when the flange 8 of the machining tool 6 is held in the container 71 as illustrated in FIG. 5, the magnetic force of the magnetic body 76 is easily transmittable to the flange 8, so that the flange 8 is attracted downward. This enables the flange 8 to be properly held in the container 71 with ease. As illustrated in FIG. 4, the thickness D21 of the intermediate member 74 is large enough to make it difficult for the magnetic force of the magnetic body 76 to be transmitted to the inner space of the intermediate member 74. Consequently, the user manually holds the machining tool 6 in the holder 64 with more ease.

In this preferred embodiment, the length D32 of the magnetic body 76 in the height direction Z is shorter than the length D31 of the magnetic body 76 in the main scanning direction Y in the front view. Thus, when the flange 8 is held in the container 71, the magnetic force of the magnetic body 76 is easily transmittable to the flange 8, so that the flange 8 is attracted downward. This enables the flange 8 to be properly held in the container 71 with ease. The length D32 of the magnetic body 76 in the height direction Z is short enough to make it difficult for the magnetic force of the magnetic body 76 to be transmitted to the inner space of the intermediate member 74. Consequently, the user manually holds the machining tool 6 in the holder 64 with more ease.

In this preferred embodiment, the intermediate member 74 includes the protrusion 74b protruding downward of the magnetic body 76. Thus, the protrusion 74b defines and functions as a guide in inserting the tool body 7 of the machining tool 6 through the third insertion hole 74a of the intermediate member 74. Accordingly, the machining tool 6 is held in the holder 64 with ease.

In this preferred embodiment, the holder 64 includes the spring 78 disposed under the magnetic body 76 and at least around the protrusion 74b of the intermediate member 74. Thus, the protrusion 74b of the intermediate member 74 defines and functions as a guide in assembling the components of the holder 64. Consequently, the spring 78 is suitably disposed under the magnetic body 76 with ease.

In this preferred embodiment, the spring 78 is made of a non-magnetic material. Thus, the spring 78 generates no magnetic force, so that the spring 78 does not attract the tool body 7 of the machining tool 6 when the user attempts to manually hold the machining tool 6 in the holder 64 of the magazine 60. Consequently, the user manually holds the machining tool 6 in the holder 64 with ease.

In this preferred embodiment, the container 71 and the intermediate member 74 are integral with each other. Alternatively, the container 71 and the intermediate member 74 may be separate components. In this case, the intermediate member 74 is preferably disposed in contact with the lower surface of the bottom plate 72a of the container 71.

In this preferred embodiment, the controller 80 drives the first motor 32A so as to cause the cutting head 40 to move along the pair of first guide rails 30 in the main scanning direction Y as illustrated in FIGS. 2 and 6. Thus, the cutting head 40 moves relative to the magazine 60 and the table 50 in the main scanning direction Y. Alternatively, the magazine 60 and the table 50 may move in the main scanning direction Y, so that the cutting head 40 moves relative to the magazine 60 and the table 50 in the main scanning direction Y.

In this preferred embodiment, the controller 80 drives the second motor 36A so as to cause the cutting head 40 to move along the pair of second guide rails 35 in the height direction Z. Thus, the cutting head 40 moves relative to the magazine 60 and the table 50 in the height direction Z. Alternatively, the magazine 60 and the table 50 may move in the height direction Z, so that the cutting head 40 moves relative to the magazine 60 and the table 50 in the height direction Z.

In this preferred embodiment, the controller 80 drives the fourth motor 50A so as to cause the table 50 and the magazine 60 to move in the sub-scanning direction X. Thus, the cutting head 40 moves relative to the magazine 60 and the table 50 in the sub-scanning direction X. Alternatively, the cutting head 40 may move in the sub-scanning direction X, so that the cutting head 40 moves relative to the magazine 60 and the table 50 in the sub-scanning direction X.

In this preferred embodiment, the magazine 60 is secured to the table 50 as illustrated in FIG. 2. Movement of the table 50 in the sub-scanning direction X causes the magazine 60 to move in the sub-scanning direction X. The magazine 60, however, does not necessarily have to be secured to the table 50. When the magazine 60 is not secured to the table 50, the magazine 60 may be connected with a motor (not illustrated), and this motor may be driven so as to move the magazine 60 in the sub-scanning direction X.

The terms and expressions used herein are used for explanation purposes and should not be construed as being restrictive. It should be appreciated that the terms and expressions used herein do not eliminate any equivalents of features illustrated and mentioned herein, and allow various modifications falling within the claimed scope of the present invention. The present invention may be embodied in many different forms. The present disclosure is to be considered as providing examples of the principles of the present invention. These examples are described herein with the understanding that such examples are not intended to limit the present invention to preferred embodiments described herein and/or illustrated herein. Hence, the present invention is not limited to the preferred embodiments described herein. The present invention includes any and all preferred embodiments including equivalent elements, modifications, omissions, combinations, adaptations and/or alterations as would be appreciated by those skilled in the art on the basis of the present disclosure. The terms and expressions in the claims are to be interpreted broadly based on the language included in the claims and not limited to examples described in the present specification or during the prosecution of the application.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A cutting apparatus for cutting a workpiece by rotating a machining tool including a rod tool body and a flange disposed on the tool body, the cutting apparatus comprising:
   a magazine including a holder to hold the machining tool; wherein
   the holder includes:
   a container to hold the flange, the container including in a bottom surface a first insertion hole through which the tool body is to be inserted;
   a magnetic body disposed under the container, the magnetic body including a second insertion hole through which the tool body is to be inserted; and
   an intermediate member disposed inside the second insertion hole of the magnetic body, the intermediate member including a third insertion hole through which the tool body is to be inserted; wherein
   assuming that a direction in which the machining tool is to be inserted into the holder is a first direction, a length of the intermediate member in the first direction is equal to or greater than a length of the magnetic body in the first direction; and the intermediate member is made of a non-magnetic material.

2. The cutting apparatus according to claim 1, wherein the container and the intermediate member are integral with each other.

3. The cutting apparatus according to claim 1, wherein the container includes:

a bottom plate provided with the first insertion hole; and
a side plate extending upward from an end of the bottom plate.

4. The cutting apparatus according to claim 3, wherein the intermediate member is connected to an underside of the bottom plate.

5. The cutting apparatus according to claim 3, wherein assuming that a direction perpendicular to the first direction in a front view is a second direction, a thickness of the intermediate member in the second direction is larger than a thickness of the bottom plate in the first direction.

6. The cutting apparatus according to claim 1, wherein assuming that a direction perpendicular to the first direction in a front view is a second direction, the length of the magnetic body in the first direction is shorter than a length of the magnetic body in the second direction.

7. The cutting apparatus according to claim 1, wherein the intermediate member includes a protrusion protruding downward of the magnetic body.

8. The cutting apparatus according to claim 7, wherein the holder includes a spring disposed under the magnetic body and at least around the protrusion of the intermediate member.

9. The cutting apparatus according to claim 8, wherein the spring is made of a non-magnetic material.

* * * * *